(12) United States Patent
Merizzi

(10) Patent No.: US 8,119,167 B2
(45) Date of Patent: Feb. 21, 2012

(54) FOOD SUPPLEMENT COMPOSITION SUITABLE FOR PROMOTING IRON ABSORPTION

(75) Inventor: Gianfranco Merizzi, Turin (IT)

(73) Assignee: Medestea Research & Production S.R.L., Colleretto Giacosa (IT)

( * ) Notice: Subject to any disclaimer, the term of this patent is extended or adjusted under 35 U.S.C. 154(b) by 1037 days.

(21) Appl. No.: 12/034,046

(22) Filed: Feb. 20, 2008

(65) Prior Publication Data

US 2008/0138436 A1 Jun. 12, 2008

Related U.S. Application Data

(62) Division of application No. 10/546,247, filed on Aug. 19, 2005, now abandoned.

(30) Foreign Application Priority Data

Feb. 20, 2003 (IT) .............................. TO2003A0126

(51) Int. Cl.
*A61K 35/32* (2006.01)

(52) U.S. Cl. .......... 424/548; 514/54; 514/494; 514/814; 530/840

(58) Field of Classification Search .................. 424/548; 514/54, 494, 814; 530/840
See application file for complete search history.

(56) References Cited

U.S. PATENT DOCUMENTS

2001/0031744 A1* 10/2001 Kosbab ........................... 514/54

OTHER PUBLICATIONS

Chan et al., Hepatic Uptake of Tc 99m MDP on Bone Scintigraphy From Intravenous Iron Therapy (Blutal), Clinical Nuclear Medicine, vol. 22, No. 11, 1997, pp. 762 764.

Kolsteren et al., Treatment for Iron Deficiency Anaemia With a Combined Supplementation of Iron, Vitamin A and Zinc in Women for Dinajpur, India, Eur. J. Clin. Nutri., vol. 53, 1999, pp. 102 106.

* cited by examiner

*Primary Examiner* — Karlheinz R Skowronek
*Assistant Examiner* — Ali Soroush
(74) *Attorney, Agent, or Firm* — Roylance, Abrams, Berdo & Goodman, L.L.P.

(57) ABSTRACT

Use of a composition comprising cartilage or chondroitin sulphate and absorbable zinc for the preparation of a food supplement or a drug suitable for promoting iron absorption in patients suffering from lack of iron.

14 Claims, No Drawings

FOOD SUPPLEMENT COMPOSITION SUITABLE FOR PROMOTING IRON ABSORPTION

This application is a divisional application of Ser. No. 10/546,247, filed Aug. 19, 2005.

The present invention relates to a food-supplement or pharmaceutical composition suitable for promoting iron absorption and to the treatment of anaemia conditions caused by lack of iron.

Lack of iron due to diets which are poor in iron or to low iron absorption by the organism is one of the primary causes of anaemia. Its therapeutic treatment is based on the administration of iron supplements such as, in particular, ferrous sulphate, with prolonged treatment required to re-establish the organism's iron reserves.

Prolonged administration of ferrous sulphate which constitutes the standard drug of reference, however, causes side effects such as gastrointestinal disorders, gastric irritation, cramps and diarrhoea which—when they arise—require a substantial reduction of the dosages.

The main problem is due to the low rate of iron absorption by the organism, which is of the order of approximately only 5-15% of the iron administered. For this reason, research relating to anti-anaemic agents for the treatment of anaemia caused by iron deficiency have been directed mainly towards the identification of preparations which can improve the solubility of iron with the use of pharmaceutical additives which improve its solubility by forming complex salts with iron, and agents such as reducing agents which can prevent oxidation of ferrous iron to ferric iron.

The present invention is based on the discovery of the fact that iron absorption can be increased by the administration of a composition comprising cartilage and absorbable zinc.

The subject of the invention is therefore the use of a composition comprising cartilage and absorbable zinc for the preparation of a food supplement or a drug which is suitable for increasing iron absorption in an individual suffering from a lack of that element and is suitable for the treatment of anaemia conditions caused by lack of iron.

In particular, the above-mentioned composition has been found suitable for promoting the absorption both of iron which is naturally present in foods and of iron which is administered—generally as a ferrous salt or complex—as a supplement in diets that are poor in iron or as a drug in the treatment of anaemia caused by lack of iron.

The cartilage which is used within the scope of the invention is generally an extract of fish cartilage, in particular cartilage of sharks or other large fish such as rays, comprising—as active ingredient—chondroitin sulphate, that is, a mixture of acid mucopolysaccharides formed by a repeating linear unit containing several sulphate groups. The basic units are constituted by N-acetyl-galactosamine and by glucuronic acid.

The use of preparations based on mucopolysaccharides or chondroitin sulphate and its salts, for example, such as sodium or potassium salts, is intended to be included within the scope of the invention.

Standardized extracts of shark cartilage are available commercially and their anti-angiogenic, anti-tumour, and anti-inflammatory activity and activity in improving skin and cartilage nutrition are already known.

The absorbable zinc is present in the composition in the form of salts with various counter-ions such as, for example, citrate, aspartate, pidolate, orotate, fumarate, gluconate, lactate, malate, succinate, picolinate, .alpha.-ketoglutarate, or mixtures thereof.

A form of zinc administration may be so-called Krebs zinc which is constituted by salified zinc with a mixture of anions formed by five primary organic acids of the Krebs cycle, that is, a mixture of zinc salts of citric, fumaric, malic, .alpha.-ketoglutaric, and succinic acids.

The cartilage extract. and the zinc may be administered, according to the invention, within the following range of dosages:

cartilage extract: 10-2000 mg/day
zinc (expressed as the ion): 5-100 mg/day.

The composition may also comprise a haematopoietic agent with anti-anaemic properties such as, in particular, folic acid, cyanocobalamin (vitamin $B_{12}$) and pyridoxine (vitamin $B_6$) and mixtures thereof with daily doses of the order of from 60 to 2000 μg/day.

In the preferred embodiment, the composition also comprises at least one anti-oxidizing agent or preferably a mixture of antioxidants which preferably comprise hydrophilic antioxidants and hydrophobic antioxidants.

The above-mentioned anti-oxidizing agents comprise:
vitamin C, typically administered in quantities of from 50 to 1000 mg/day,
vitamin E, typically administered in quantities of from 5 to 500 mg/day, and
bioflavonoids, containing proanthocyanidin and terpene compounds.

The preferred sources of bioflavonoids or of terpene compounds in the composition of the invention comprise natural extracts such as, in particular:

extract of *Vitis vinifera* (containing leucocyanidin or leucoanthocyanin), comprising procyanidolic oligomers, typically dimers, trimers, tetramers, pentamers and heptamers produced by condensation of monomeric units of flavan-3-ols and flavan-3,4-diols, free or esterified with gallic acid;

extract of *Centella asiatica* obtained by extraction and purification of the aerial part of *Centella asiatica* (asiatic hydrocotyl), typically comprising a terpenic mixture of madecassic acid (about 30%), asiatic acid (about 30%) and asiaticoside (about 40%);

standardized extract of *Ginkgo biloba* comprising bioflavones, flavonolglucosides and lactonic terpenes.

The above-mentioned extracts may be used in association in the composition according to the invention and may optionally be standardized extracts in complexed form with phospholipids to improve bio-availability.

Typical dosages of these extracts in the composition of the invention are of the order of from 10 to 500 mg/day.

Further anti-oxidizing agents that may be used comprise lipoic acid and lycopene.

The presence of the above-mentioned anti-oxidizing agents—and particularly of the bioflavonoid-based antioxidants—may be considered synergic in increasing iron absorption by favouring the presence of reduced iron which is that which is most easily absorbed.

The invention includes within its scope both iron-free compositions and compositions including iron—generally as ferrous ion—the combined use of which is rendered necessary when the lack of iron in the patient undergoing treatment is also due to a diet that is poor in iron. It is intended that the administration of iron supplements may be performed in association with the composition according to the invention or in combined treatment.

If the administration of iron is associated with the composition according to the invention, the composition may typically comprise doses of the order of from 5 to 300 mg/day of iron, as the ferrous ion, for example, as ferrous sulphate or other salts such as, in particular, aspartate, citrate, picolinate, ascorbate, gluconate, fumarate and salicylate.

The composition according to the invention may also comprise active ingredients selected from eicosapentaenoic acid (EPA) docahexanoic acid (DHA), .gamma.-linolenic acid, and mixtures thereof. As the source of eicosapentaenoic acid and docahexanoic acid, the use of fish oil or microalgae oil is preferable and, as the source of .gamma.-linolenic acid, the use of borage oil or evening primrose oil is preferred.

The composition according to the invention is formulated in a form suitable for oral administration, in particular as soft-shell or rigid-shell gelatine capsules, tablets, pills, elixirs, suspensions, and syrups.

The activity of the composition in promoting iron absorption has been confirmed by clinical tests on twenty female patients with levels of sideraemia below the threshold value.

Four capsules each of 800 mg were administered to the twenty patients under test for thirty days; the capsules comprised:
 shark cartilage extract: 300 mg/cps
 zinc (expressed as the ion): 7.5 mg/cps
 folic acid: 50 µg/cps
 extract of *Centella asiatica:* 20 mg/cps
 extract of leucocyanidin (*Vitis vinifera*): 50 mg/cps
 vitamin E: 15 mg/cps
 fish oil: 120 mg/cps
 borage oil: 240 mg/cps.

During the period of treatment the patients were required to maintain a normal diet which was confirmed not to be lacking in iron.

Upon completion of the treatment, the twenty patients under test had sideraemia values greatly above the threshold value.

The following table gives the sideraemia values as mean initial values, final values and normal values.

|  | Mean initial values | Mean final values | Normal values |
|---|---|---|---|
| Sideraemia | 38 mcg/dl | 75 mcg/dl | 50-160 mcg/dl |

What is claimed is:

1. A method for enhancing iron absorption in a patient suffering from lack of iron by administering to said patient an effective amount of an iron-free composition comprising: (a) cartilage or chondroitin sulphate, and (b) absorbable zinc, each being present in a concentration suitable for promoting iron absorption in treated patients.

2. The method according to claim 1 wherein the patient suffers from anemia caused by lack of iron.

3. The method according to claim 1 in which said composition comprises cartilage and zinc, and said composition is administered at a rate sufficient to provide a cartilage administration rate within the range of from 100 to 2000 mg/day and the zinc, expressed as the ion, is administered at a rate of from 5 to 100 mg/day.

4. The method according to claim 1 in which the cartilage is a standardized shark cartilage extract.

5. The method according to claim 1 in which the absorbable zinc in said composition is administered in the form of a salt selected from the group consisting of citrate, fumarate, gluconate, α-ketoglutarate, lactate, malate, succinate, picolinate, aspartate, pidolate, orotate, and mixtures thereof.

6. The method according to claim 1 in which the composition further comprises a haematopoietic agent selected from the group consisting of folic acid, vitamin $B_6$ and vitamin $B_{12}$.

7. The method according to claim 6 in which the haematopoietic agent is included in the composition for administration within the range of from 60 to 2000 µg/day.

8. The method according to claim 1 in which the composition further comprises at least one anti-oxidizing agent selected from the group which consists consisting of vitamin E, vitamin C, bioflavonoids, terpenes, lycopene, lipoic acid, and mixtures thereof.

9. The method according to claim 8 in which the bioflavonoid-based anti-oxidizing agent comprises a vegetable extract selected from the group consisting of extract of *Vitis vinifera*, extract of *Ginkgo biloba*, extract of *Centella asiatica*, and mixtures thereof.

10. The method of claim 1 wherein said iron-free composition is administered in an amount effective to treat anemia and promote absorption of iron naturally present in foods, and where said iron-free composition is administered in the absence of iron supplements, ferrous salts or ferrous complexes.

11. A method for enhancing iron absorption from foods comprising: administering to a patient suffering from a lack of iron a composition in an amount effective to enhance absorption of iron naturally found in foods consumed by said patient, said composition being an iron-free composition comprising (a) cartilage or chondroitin sulphate, and (b) absorbable zinc, each being present in an amount effective to promote iron absorption from foods by said patient.

12. The method of claim 11 wherein said iron-free composition further comprises an antioxidant in an amount to provide a synergistic effect in enhancing iron absorption from food.

13. A method of treating anemia in a patient caused by a lack of iron without administering ferrous salts or ferrous complexes to said patient, said method comprising the step of enhancing absorption of iron naturally present in foods of the patient's diet, by administering to said patient an effective amount of an iron-free composition comprising (a) cartilage or chondroitin sulphate, and (b) absorbable zinc, each being present in an amount effective to promote iron absorption from food in the patient's diet.

14. The method of claim 13 wherein said composition further comprises an antioxidant in an amount effective to provide a synergistic effect in enhancing iron absorption from food.

\* \* \* \* \*